(12) United States Patent
Olcott et al.

(10) Patent No.: US 8,946,656 B2
(45) Date of Patent: Feb. 3, 2015

(54) METHODS AND SYSTEMS FOR RADIATION DETECTION

(75) Inventors: Peter D. Olcott, Stanford, CA (US); Craig S. Levin, Palo Alto, CA (US)

(73) Assignee: The Board of Trustees of The Leland Stanford Junior University, Stanford, CA (US)

( * ) Notice: Subject to any disclaimer, the term of this patent is extended or adjusted under 35 U.S.C. 154(b) by 154 days.

(21) Appl. No.: 13/018,310

(22) Filed: Jan. 31, 2011

(65) Prior Publication Data

US 2011/0204241 A1    Aug. 25, 2011

Related U.S. Application Data

(60) Provisional application No. 61/299,921, filed on Jan. 29, 2010.

(51) Int. Cl.

| | |
|---|---|
| *G01J 1/58* | (2006.01) |
| *G01N 21/00* | (2006.01) |
| *G01T 1/20* | (2006.01) |
| *G01T 1/29* | (2006.01) |

(52) U.S. Cl.
CPC .................................. *G01T 1/2985* (2013.01)
USPC ............... 250/487.1; 250/363.03; 250/474.1; 250/368

(58) Field of Classification Search
USPC ................. 250/363.03, 474.1, 368, 487.1
See application file for complete search history.

(56) References Cited

U.S. PATENT DOCUMENTS

| | | | |
|---|---|---|---|
| 6,218,673 B1 * | 4/2001 | Gore et al. ................. | 250/474.1 |
| 2003/0218138 A1 * | 11/2003 | Sharma ...................... | 250/474.1 |
| 2005/0171438 A1 * | 8/2005 | Chen et al. .................... | 600/476 |
| 2006/0202125 A1 | 9/2006 | Suhami | |
| 2009/0093710 A1 | 4/2009 | Levin | |

OTHER PUBLICATIONS

Derenzo, SE, "Design and Implementation of a Facility for Discovering New Scintillator Materials (2008)", LBL Report 753E: http://repositories.cdlib.org/lbnl/LBNL-753E.

Iwano, Kaoru, "Theory for photoinduced phase transition from a charge-density-wave state to a Mott-Hubbard insulator in a quasi-one-dimensional Br-bridged Pd compound", Phys. Rev. B, 2004; 70(24): 241102-241106.

Koshihara, S, "Photo-induced phase transition: From where it comes and to where it goes?", Journal of Physics—Conference Series, 2002; 21(7):1742-6588.

(Continued)

*Primary Examiner* — David Porta
*Assistant Examiner* — Kenneth J Malkowski
(74) *Attorney, Agent, or Firm* — Greer, Burns & Crain, Ltd.

(57) ABSTRACT

An apparatus for detecting ionizing radiation from a source. A detector is disposed relative to the source to receive the ionizing radiation. The ionizing radiation causes ionization and/or excitation in the detector, wherein an optical property of the detector is altered in response to the ionization and/or excitation. A source of coherent probing light is disposed relative to the detector to probe the detector. The detector outputs the probing light, wherein the output light is modulated in response to the altered optical property. A receiver receives the output light and detects modulation in the output light.

8 Claims, 12 Drawing Sheets

(56) References Cited

OTHER PUBLICATIONS

Olcott, Peter D.; et al., "Novel electro-optically coupled MR-compatible PET detectors", Nuclear Science Symposium Conference Record, 2008. NSS '08. IEEE, vol., No., pp. 4640-4645, Oct. 19-25, 2008.

Qi, Minghao, et al., "A three-dimensional optical photonic crystal with designed point defects", Nature 2004; 429:538-542. [6] R. M. Osgood; et al. Engineering nonlinearities in nanoscale optical systems: physics and applications in dispersion-engineered silicon nanophotonic wires, Adv. Opt. Photon. 1, 162-235 (2009).

Shinya, A., et al., "All-optical on-chip bit memory based on ultra high Q InGaAsP photonic crystal", Opt. Express 16, 19382-19387 (2008).

Surti, S., et al., "Investigation of time-of-flight benefit for fully 3-D PET", IEEE Trans Med Imaging. May 2006;25(5):529-38.

Tomimoto, Shinichi, "Ultrafast dynamics of lattice relaxation of excitons in quasi-one-dimensional halogen-bridged platinum complexes", Phys Review B 2002; 66:155112.

Yamawaki, Masato, "A Study of Reflection and Connection Materials used for Transmitting and Condensing Scintillation Light by means of Optical Fiber", Joint International Workshop: Nuclear Technology and Society—Needs for Next Generation, Berkeley, California, Jan. 6-8, 2008, Berkeley Faculty Club, UC Berkeley Campus.

\* cited by examiner

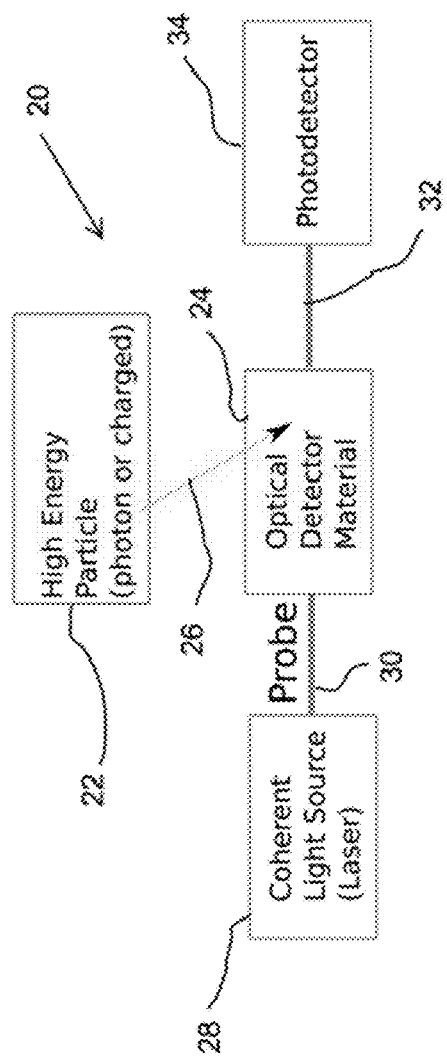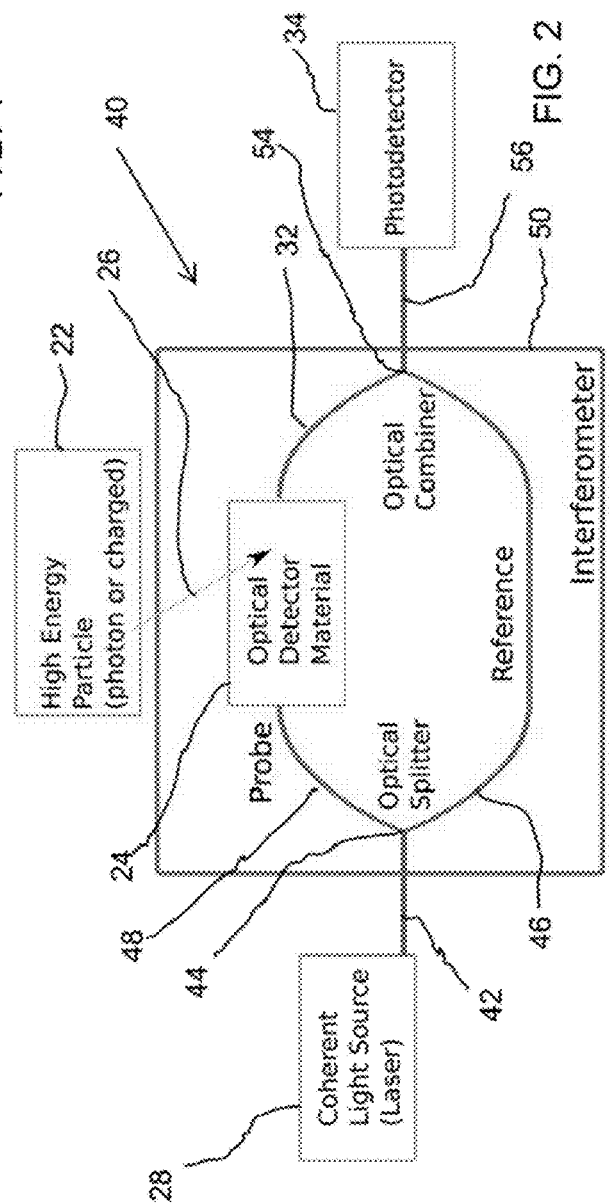

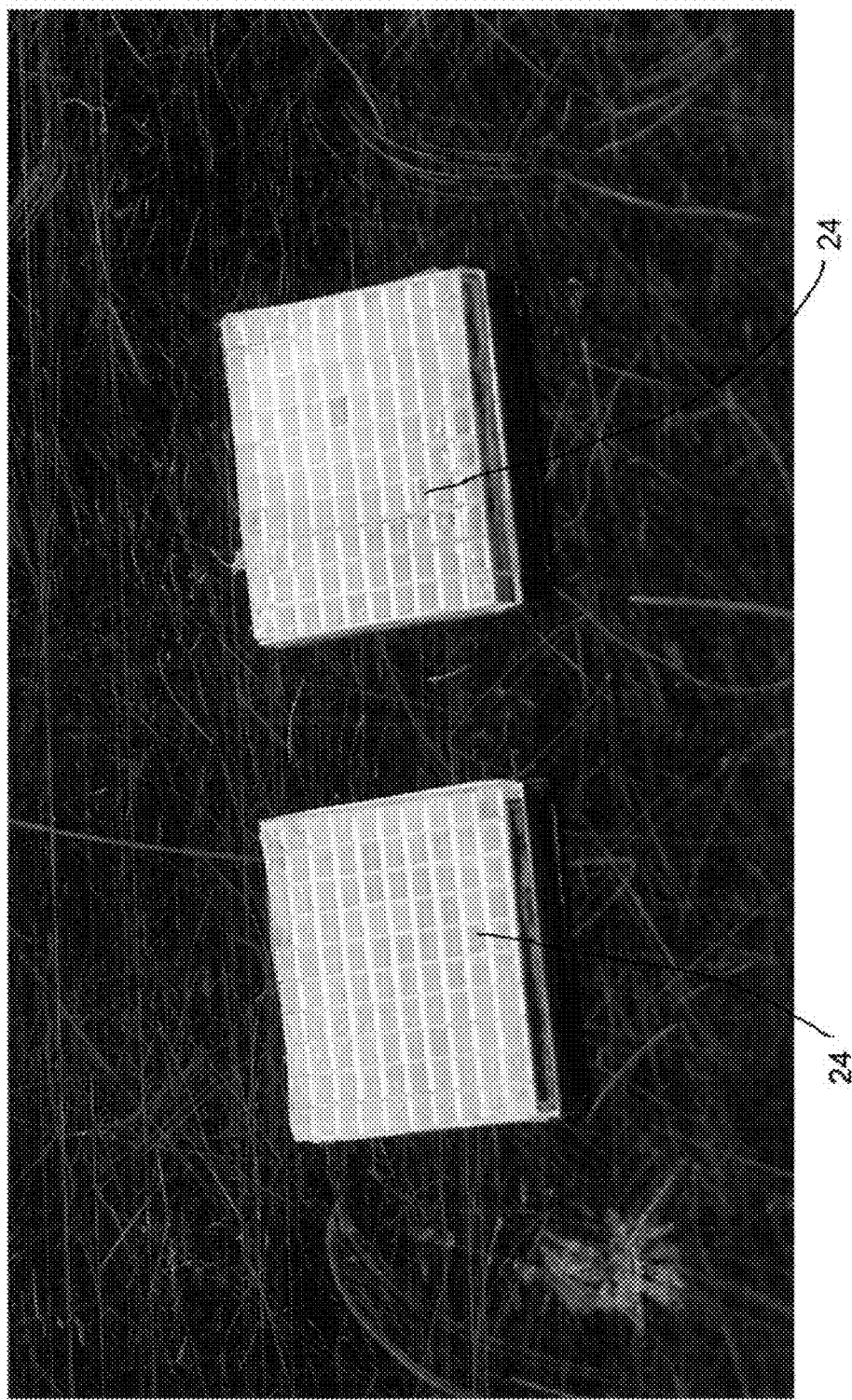

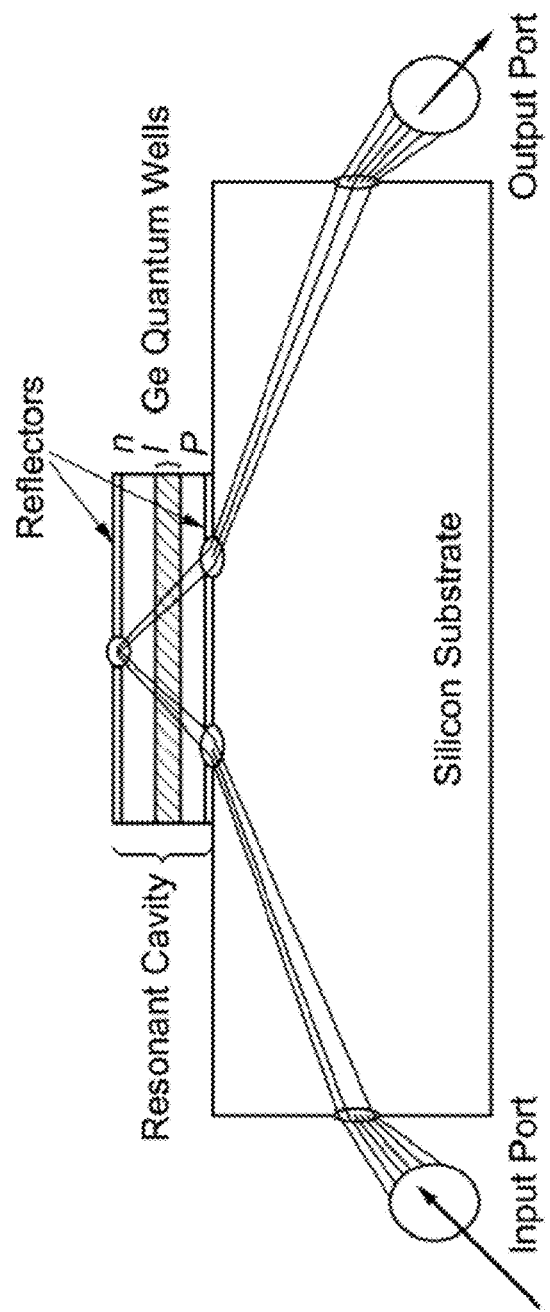

METHODS AND SYSTEMS FOR RADIATION DETECTION

PRIORITY CLAIM AND REFERENCE TO RELATED APPLICATION

This application claims the benefit of U.S. Provisional Application Ser. No. 61/299,921, filed Jan. 29, 2010, under 35 U.S.C. 119, and which application is incorporated by reference herein.

FIELD OF THE INVENTION

This invention relates generally to the field of ionizing radiation detection, including gamma ray detection and beta detection. More particular example embodiments of the invention relate to imaging, such as positron emission tomography (PET).

BACKGROUND OF THE INVENTION

It is useful in many applications to detect ionizing radiation. Applications for detecting ionizing radiation include, but are not limited to, imaging, nuclear detection, particle physics, gamma ray astronomy, nuclear non-proliferation and homeland defense.

As one nonlimiting example application, positron emission tomography (PET) is a non-invasive imaging technology that enables visualization and quantification of the molecular signatures of disease in living subjects in a clinic as well as in animal research. In clinical use, PET is standard-of-care for diagnosis, staging, and monitoring treatment for many types of cancers. The method involves injection of a trace amount of a radioactively-labeled chemical, referred to as the molecular probe, into the subject. The label is a type of radionuclide that emits positrons. Ideally, the probe is taken up in the cells of tissues in proportion to the presence of the molecular signature of disease. For clinical management of cancer, the most common probe used is a radioactive analog of glucose, known as 18F-fluorodeoxyflucose (FDG), and the cancer signature is an up-regulation of cellular glycolysis.

In an example imaging method the patient is placed in a PET scanner, comprising a ring or cylinder arrangement or various other arrangements of high-energy photon detector elements, typically photon sensors known as scintillation crystal detectors (scintillation detectors), and supporting electronics, which makes a quantitative image of the probe biodistribution. The radionuclide attached to the probe molecule emits a positron, which subsequently annihilates with a nearby electron, yielding two oppositely directed photons, each having energy of 511 kilo-electron-Volt (keV), the rest mass energy of the electron (or positron). The two annihilation photons are emitted from the body and detected nearly simultaneously in two small opposing detector elements that localize each photon's point of entry into the system as well as measure their energy and arrival time. If two photons on opposite sides of the system arrive within a selected coincidence time window setting, it is assumed that they came from the same positron decay event. This coincidence detection process localizes each positron decay event, and thus the molecule of interest, to somewhere along the line of response (LOR) extending between two detector elements. Successively detected coincident photon events are aggregated throughout the PET system over a period of time, for instance ~30 minutes. Then, mathematical statistical likelihood algorithms, typically based on the framework of maximum likelihood estimation maximization (MLEM), are used to reconstruct three-dimensional (3-D) images of the probe biodistribution that most likely created the pattern of many two-photon hits recorded by the scanner.

These algorithms involve computationally intensive back and forward line-projection operations along each LOR through the 3-D image volume. Further, conventional PET can exhibit less than desirable signal-to-noise ratio (SNR) in the reconstructed images.

Significant research has focused on improving the scintillation crystal of the detector to go beyond simple coincidence detection capability to time-of-flight (ToF) capability. In ToF-PET, in addition to being able to determine to which detector LOR the event belongs, the detector coincidence time resolution is high enough to enable one to constrain the two photon emission point to within a particular segment along that line. However, in known ToF PET systems, timing resolutions tend to drift with time and suffer from count rate limitations. While improved ToF-PET systems have demonstrated improved lesion contrast and image SNR for larger patients, little or no image SNR benefit is provided for smaller patients or for small animal imaging.

SUMMARY OF THE INVENTION

Embodiments of the present invention provide, among other things, an apparatus for detecting ionizing radiation from a source. The apparatus comprises a detector disposed relative to the source to receive the ionizing radiation. The ionizing radiation causes ionization and/or excitation in the detector, wherein an optical property of the detector is altered in response to the ionization and/or excitation. A source of light is disposed relative to the detector to probe the detector. The detector outputs the probing light, wherein the output light is modulated in response to the altered optical property. A receiver is provided for receiving the output light and detecting modulation in the output light.

BRIEF DESCRIPTION OF THE DRAWINGS

FIG. 1 shows an apparatus for detecting ionizing radiation from a source, according to an embodiment of the present invention;

FIG. 2 shows an apparatus for detecting ionizing radiation from a source including a comparator, according to another embodiment of the present invention;

FIGS. 4A-4B are perspective views of an example arrangement of photonic detector elements;

FIG. 5A shows conventional positron emission tomography (PET), FIG. 5B shows time-of-flight (ToF) PET, and FIG. 5C shows <30 ps time resolution ToF PET according to an embodiment of the present invention;

FIGS. 9A-9B show a scanning electron micrograph (SEM) of a fabricated 1.3 µm InGaAsP core PhC on InP substrate, and FIG. 9C is a schematic view of a cavity, where the core thickness and air hole diameter are 200 and 2000 nm, respectively, the lattice constraints are 420–440 nm, and air holes surrounding a cavity are shifted away from the center of the line defect by distances of 9, 6, and 3 nm, respectively;

FIGS. 10A-10B show a quantum confined stark effect device for use as an optical modulator for PET signals. The direct ionization from a high energy photon creates an electric field such that it modulates the band-edge of the device which in turn modulates the optical property of absorption. FIG. 10A shows single quantum dot (QD) Stark spectra under applied modulation: (A) Emission spectra of a single QD from the 37.5 Å ZnS-overcoated sample under conditions of alternating electric field. Frames indicate the applied field in kilovolts per centimeter. (B) Seventeen spectra of the same single QD under a range of electric fields. Frames indicate the applied field in kilovolts per centimeter and the magnification of the y axis. (C) Plot of Stark shift versus electric field for the spectra in (B). The line represents a fit to the sum of a linear and quadratic shift as a function of field. The excitation intensity for all spectra in (A) and (B) was 25 W/cm2, and taken from Empedocles, et al, "Quantum-confined Stark effect in single CdSe nanocrystallite quantum dots." Science (1997). FIG. 10B is a Germanium quantum well disposed on a silicon substrate taken from Miller, "Germanium Quantum Wells for High-Performance Modulators in Silicon Photonics," Photonics Spectra (2007)

DETAILED DESCRIPTION

Embodiments of the present invention provide, among other things, an apparatus for detecting ionizing radiation from a source. "Radiation" as used herein refers to energetic photons or other types of particles that can interact with crystal materials for their detection. "Ionizing radiation" refers to such particles having an energy greater than the outer shell atomic electron binding energies of the matter traversed, but is typically >1 keV.

An example apparatus allows detection of ionizing radiation with a very high time resolution (e.g., as high as on the order of femtoseconds). A nonlimiting example source is a source of emitted photons, such as a radioactive material in the form of a molecular probe that has been introduced into a subject. The source may include a positron emission source. Nonlimiting examples of ionizing radiation include gamma rays, X-rays, beta rays, alpha rays, and annihilation photons.

Figure 10A:
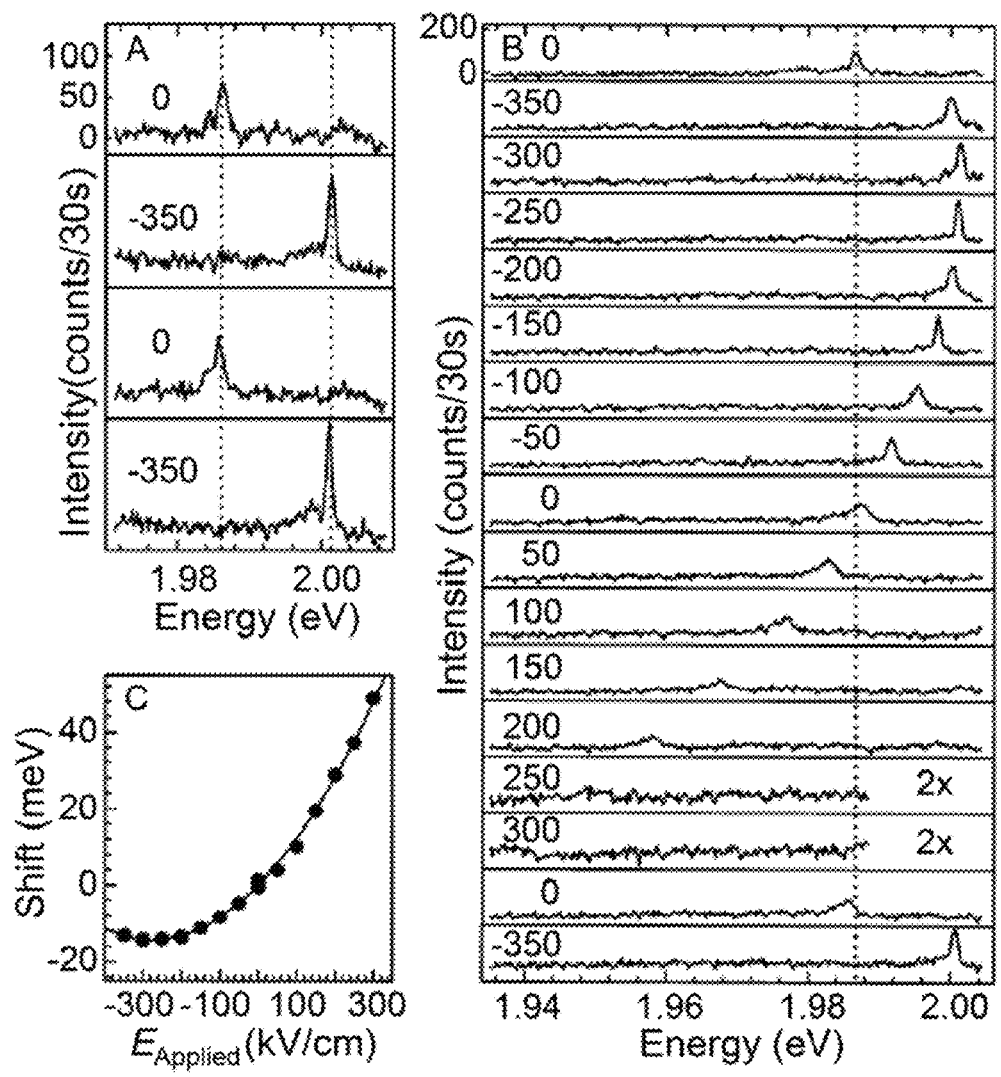

At least one detector is disposed relative to the source to receive the ionizing radiation. The at least one detector includes a material for which the received ionizing radiation causes ionization or excitation in that material, and for which the ionization or excitation in that material causes an optical property to be altered. A nonlimiting example material is a nonlinear photonic material, though this is not required. It is desired for the material to have a high density and a high Z (or average atomic number) for better interaction probability of incoming ionizing radiation, while being alterable in an optical property in response to interaction with the ionizing radiation (e.g., able to convert the ionizing radiation to an electron-hole pair cloud as well as forms of excitation energy within the material). A particular example material is a platinum bromide complex, such as a quasi-one-dimensional halogen-bridged platinum complex. Nonlimiting example materials that may be used for the detector are discussed in Shinichi Tomimoto, Ultrafast dynamics of lattice relaxation of excitons in quasi-one-dimensional halogen-bridged platinum complexes, Phys Review 13, 2002; 66:155112, the entirety of which is incorporated by reference herein. If the detector material is used for PET, the crystals should be relatively thick, as well. Another particular example material is a quantum-confined Stark effect created in an engineered CdSe quantum dot discussed in Empedocles, et al, "Quantum-confined Stark effect in single CdSe nanocrystallite quantum dots." Science (1997) (FIG. 10A). This quantum dot is of higher atomic Z than silicon and can be assembled in such a way to make a thick detector. The quantum confined stark effect can also be fabricated in solid semiconductors such as on top of silicon as described in "Germanium Quantum Wells for High-Performance Modulators in Silicon Photonics," Photonics Spectra (2007) (FIG. 10B). Germanium quantum wells can be fabricated and probed in such a manner that they are sensitive to high energy ionizing radiation.

The optical properties of the detector that can be altered in response to ionization and/or excitation (e.g., an electron-hole cloud, vibration energy, or heat) may include, but are not limited to, refraction (e.g., index of refraction as a function of wavelength), reflectance, absorption, polarization (e.g., polarization of a light wave, modulated either proportionally or a binary modulation, either discrete or continuous, and altering polarization may also include alteration of absorption, index of refraction, reflectance as a function thereof), and/or phase of light. These properties may be altered individually or in combination, proportionally or in a binary fashion. As a nonlimiting example, the reflectance of a platinum bromide complex can be altered by ionization electrons and/or holes produced by receiving ionizing radiation. As another nonlimiting example, the absorption of a quantum confined Stark effect electro-optical modulator can be altered by the ionization electron and/or holes produced by receiving ionizing radiation.

The apparatus further includes a source of probing light and preferably, though not necessarily, a source of reference light. The probing light and reference light may be either pulsed or not pulsed (e.g., a continuous laser or continuous wave (CW) laser). Preferably but not necessarily, the probing light and reference light are coherent light (i.e., the photons are in phase with one another), and the source of probing light and the source of reference light may be a laser. The wavelength, and if pulsed, the rate of the probing light and reference light may be carefully selected to improve detection.

The source of probing light is disposed relative to the at least one detector to probe the detector, such as by introducing the probing light into the detector (e.g., by shining the probing light on the detector). In operation, the probing light enters the detector, wherein it passes through the detector before being output. The output light is modulated in response to the altered optical property; that is, in response to the ionization or excitation caused by the ionizing radiation interacting with the detector. Thus, in an example operation, the electron-hole cloud created by the ionization alters one or more of the detector's optical properties, and in turn modulates the output light, producing a change in the output light. This change can be detected by an apparatus to determine that the ionizing radiation has interacted with the detector.

Other example apparatus and methods of the present invention provide an imaging system and method using inventive methods for detecting ionizing radiation. The greatly improved time resolution provided by example detectors, detector systems, and/or methods allows significantly improved resolution (e.g., reduced or eliminated blurring) for a particular amount of imaging time and/or a significantly reduced imaging time for a particular image resolution. Photonic materials, especially ones that can modulate coherent light, have conventionally not been used for high energy photon (e.g., 511 keV) detectors.

Thus, in a nonlimiting example imaging method incorporating inventive methods for detecting ionizing radiation to time-of-flight (ToF) PET, the total transit time across a patient may be about two and a half nanoseconds, providing a similar coincidence time window. Due to the improved time resolution, the confined origin of annihilation photon emission in ToF PET along any given LOR can be narrowed to pinpoint the precise annihilation photon emission location (e.g. single image voxel) by following the LOR between the two detected interactions and considering the speed of light. Such defined emission point locations along many system detector response lines can in turn be aggregated by a processor, followed by the image reconstruction process to provide an image.

Such imaging systems and methods provide a clear advantage of essentially restricting event positioning to a point versus a line segment and thus reducing the amount of imaging time needed, as less data is required by collecting specific points versus collecting line segments for use in image reconstruction methods such as, but not limited to, MLEM image reconstruction methods. This higher image count density per time in turn can significantly reduce the amount of time or, alternately, injected radiation dose needed for a patient being imaged. Further, the processing needed at the receiver can be significantly reduced. Alternately, the boost in image SNR may be exploited to better detect subtle concentrations of the probe above background, for example, in early disease detection.

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

FIG. 1 shows an apparatus 20 for detecting ionizing radiation from a source 22 according to an embodiment of the present invention. As a nonlimiting example, the source 22 is a source of high energy particles (e.g., photon or charged particle). The apparatus 20, as a nonlimiting example, can be an imaging system. A detector 24, which can be embodied in one or several detectors including optical detector material, is disposed relative to the source to receive ionizing radiation 26. The ionizing radiation 26 causes ionization and/or excitation in the detector 24, causing an optical property of the detector to be altered in response.

To detect this change in optical property, a source of light, and preferably coherent probing light 28, is disposed relative to the detector 24 to probe the detector, such as by generating an input probing light 30. Optical fibers may be used to couple the source of probing light 28 to the detector 24. A suitable input lens (not shown), such as but not limited to a collimation lens, may also be provided between the source of probing light 28 and the detector 24 for tightly collimating the light. Collimating the light helps maintain the light coherence for more accurately determining change in the probing light.

The detector 24 outputs the probing light, such as via output light 32, and this output light is modulated in response to the altered optical property produced by the ionizing radiation 26. An output lens (not shown), such as but not limited to a collimation lens, may be provided in an optical path of the output of the detector 24. Both the input and output lenses can be coupled to suitable optical couplings, e.g., optical fibers, and may be coupled to the detector 24 in a manner analogous to lenses for solid state lasers.

A receiver is provided for receiving the output light 32 and detecting modulation in the output light. In the example apparatus 20 shown in FIG. 1, a receiver includes a photodetector 34 that detects a change in the output light 32 from the detector 24 without a reference light. For example, the photodetector 34 can receive output light 32 before and after modulation and determine when the output light has been modulated.

Thus, in the example apparatus 20 of FIG. 1, the coherent light source 28 probes the optical detector material of the detector 24, and the output light 32 from the optical detector material is detected by the photodetector 34. The output light 32 is modulated based on a change in an optical property of the optical detector material due to interaction with the high energy particle (photon or charged particle) 26 from the source 22. Detecting the modulation in the output light 32 in turn detects the high energy particle interaction.

The detector 24 can include a plurality of detectors, and the receiver can include a plurality of receivers. As a nonlimiting example, if the apparatus 20 is to be used for detecting a pair of photons in coincidence, at least one detector and receiver can be provided for detecting each of the pair of photons.

In another example apparatus, a source of reference light can be provided, and the reference light can be used to help detect the change in the output light caused by modulation. For example, in the apparatus 40 shown in FIG. 2, where like parts are represented by like reference characters, the source of reference light, as a nonlimiting example, may be an output light 42 from the coherent light source (e.g., a laser) that is split by an optical splitter 44 to provide both a source of reference light 46 and a source of probing light 48. In a nonlimiting embodiment, if the probing light 48 and the reference light 46 are coherent, (e.g., phase and/or polarization coherent), any modulation of the probing light 48 via the detector 24 can be easily detected by comparing the output probing light and the reference light. The coherent light provides a balance between the probing light 48 and the reference light 46, allowing easier detection of changes. However, a comparison is also possible if the probing light 48 or the reference light 46 is not coherent light (e.g., an LED), though the time resolution performance may be significantly reduced.

In a nonlimiting example embodiment, a comparison of the output light 32 from the detector 24 to the reference light 46 is provided in an optical realm by a comparator, such as but not limited to an interferometer 50. A nonlimiting example of an interferometer is a Mach-Zehnder interferometer. The interferometer 50 preferably is coupled to the output probing light 32 and to the reference light 46 by suitable optical coupling, including but not limited to optical fiber. A separate interferometer 50 may be used for each channel (e.g., detector or detector face), and/or channels may be multiplexed. The coupling may also include output or input lenses as described above. Nonlimiting examples of suitable optical coupling are provided in Olcott, Peter D., Peng, Hao, and Levin, Craig S., "Novel electro-optically coupled MR-compatible PET detectors," Nuclear Science Symposium Conference Record, 2008, NSS '08, pp. 4640-4645 19-25 Oct. 2008, and in U.S. patent application Ser. No. 12/246,326, filed Oct. 6, 2008, both of which are incorporated by reference herein. Other methods of optical coupling are also possible. The optical coupling may be for individual detectors, and/or output light or reference light sources may be multiplexed for reducing the number of optical channels needed. The optical coupling preferably includes stable materials, examples of which will be appreciated by those of ordinary skill in the art.

In a particular nonlimiting example of the apparatus 40 shown in FIG. 2, the interferometer 50 or interferometers also provide(s) both the optical splitter 44, to provide both the reference light 46 and the (input) probing light 48, and an optical combiner 54 for combining the reference light and the output probing light 32 from the detector 24, and thus a single element may be used for both components. An example of this is a two-to-one combiner or splitter, of which the Mach-Zehnder interferometer is a nonlimiting example. Other methods or devices for splitting, combining, and/or comparing may be used, however.

The comparator (e.g., interferometer 50) is configured in example embodiments to provide an output pulse 56 based on a change between the reference light 46 and the output probing light 32. This output pulse 56 can be detected by a receiver such as the photodetector 34 to detect modulation in the output light 32. It is also contemplated for all embodiments that the detector 34 could be an all-optical detector, with/ without optical processing. Generally, a receiver refers to a device that receives the output light 32 from the detector 24, directly or indirectly, and detects modulation in the output light. Thus, the comparator, such as the interferometer 50, and/or the photodetector 34 or other detector, can be considered a receiver or components of a receiver, depending on the particular embodiment.

In another nonlimiting example, a phase shift, e.g., an optical phase shifter (not shown in FIG. 2), may be introduced between the reference light 46 and the combiner 54. The phase shift may be, for instance, a 180 degree phase shift. If the reference light 46 and the output probing light 32 are the same (or substantially the same, to within the resolution of the interferometer 50 and/or a selected threshold for detection), as can occur if the material of the detector 24 is not hit by the ionizing radiation 26, the combined light can (or can be made to) cancel. In other words, in this (non-modulated) case the probing light 48 would go substantially unperturbed through the material of the detector 24 and output via the optical coupling, where it interferes with the reference light 46.

On the other hand, when the ionizing radiation 26 interacts with the material in the detector 24, the optical property or properties is/are changed, causing the detector to modulate the probing light 48 in some way (e.g., attenuates some of the light, reflects some of the light, delays the light, speeds up the light, etc.). Any of these (and other) types of modulation provide a change in the output probing light 32 with respect to the reference light 46. The interferometer 50 provides an output pulse 56 based on this change, which can be detected by detector 34. As a nonlimiting example, by subtracting the output probing light 32 from the reference light 46 (or vice versa), the difference can be represented by the output pulse 56.

Figure 3:
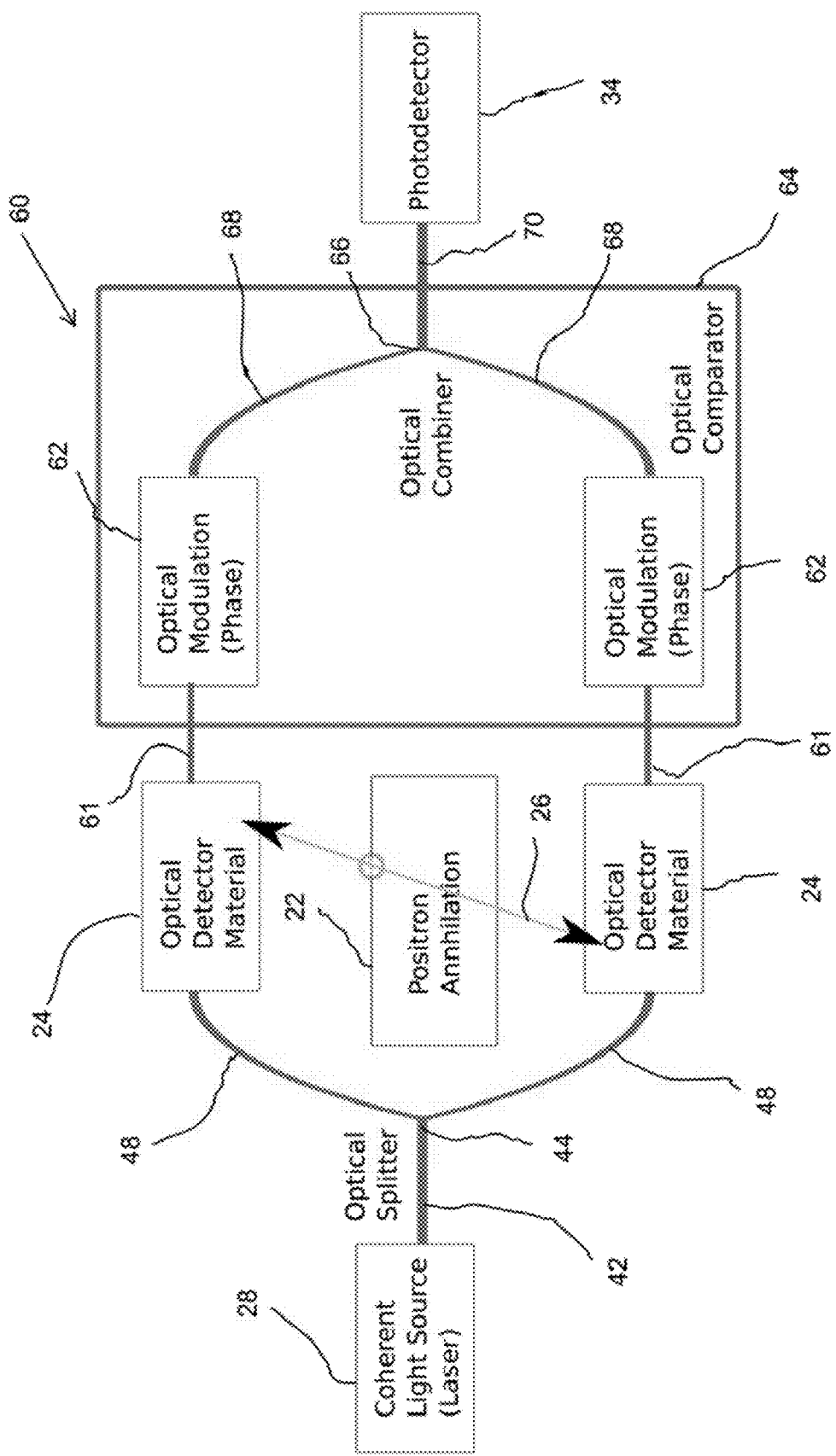
FIG. 3 shows an apparatus for detecting ionizing radiation from a source including an optical splitter and optical comparator for a coherent light source, according to another embodiment of the present invention.

Alternatively, as shown in the apparatus 60 in FIG. 3, where like parts are represented by like reference characters, an output 61 of other detector(s) 24 can be considered a "reference" light if it is suitably phase shifted by a phase shifter, such as optical phase shifter 62. An optical comparator 64, e.g., an interferometer, includes an optical combiner 66 for combining the phase-shifted outputs 68 and produces an output pulse 70. The output pulse 70 from the comparator 64 represents whether an ionizing radiation interaction with that detector 24 occurred with very high time resolution.

A suitable receiver coupled, directly or indirectly, to the interferometer 50, comparator 64, and/or the detector 24, receives and reads the output 32 and/or the output pulse 56, 70 (e.g., reads a front end or initial change of an output pulse over a certain threshold) and records the time and the detector 24 that was hit. A nonlimiting example receiver includes a detector for the output pulse, e.g., the photodetector 34 or an array of photodetectors (for a plurality of detectors), and a processor for processing the received output pulses and determining the detector crystal that was hit and the absolute time of arrival. These hit detector crystals and arrival times may then be histogrammed, or subjected to further processing and then histogrammed. Nonlimiting example receivers include high speed infrared GaAs PIN diodes. Nonlimiting example processors, which may be separate from or combined with the receiver, include any computer or computing device programmed (e.g., in software, hardware, firmware, via a non-transitory medium containing executable instructions, etc.) to perform example methods of the invention. If the processing is performed entirely within the optical realm, a photonic optical processing engine may be used, having suitable processing properties (e.g., image formation and processing, and as a more particular example PET coincidence processing) for optics. However, it will be appreciated that other types of imaging may be provided, such as but not limited to SPECT, PET, and other methods for gamma ray and beta imaging.

In addition to the Mach-Zehnder interferometer, other comparators are possible for comparing the reference light 46 and the output probing light 32, 61. Further, other detectors are possible for detecting a change in the output light. As another example, an intensity detector, such as a photodiode(s), can be used. In a nonlimiting example, the output probing light 32 can be focused directly into the photodiode, as represented by the photodetector 34 shown in FIG. 1, so that altering reflectance or transmission of the optical detector material 24 by interacting with the ionizing radiation 26 will change the intensity of the probing laser 30. If the output intensity is measured as a function of time, the change will be detectable, though it may be less sensitive than using an interferometer, because the electrical realm is entered. The interferometer 50, on the other hand can provide time resolution on the order of femtoseconds, providing a very good estimation of timing arrival.

Among other applications, the apparatus 20, 40, 60 according to embodiments of the present invention can be used for imaging of ionizing photons. The greatly improved time resolution provided by the example detectors and detection system allows for improved time and (in some embodiments) spatial resolution for annihilation photon or gamma ray imaging, while avoiding many of the complex algorithms needed for conventional imaging. The received detector locations and interaction times can be histogrammed and processed to provide an image.

Figure 4B:
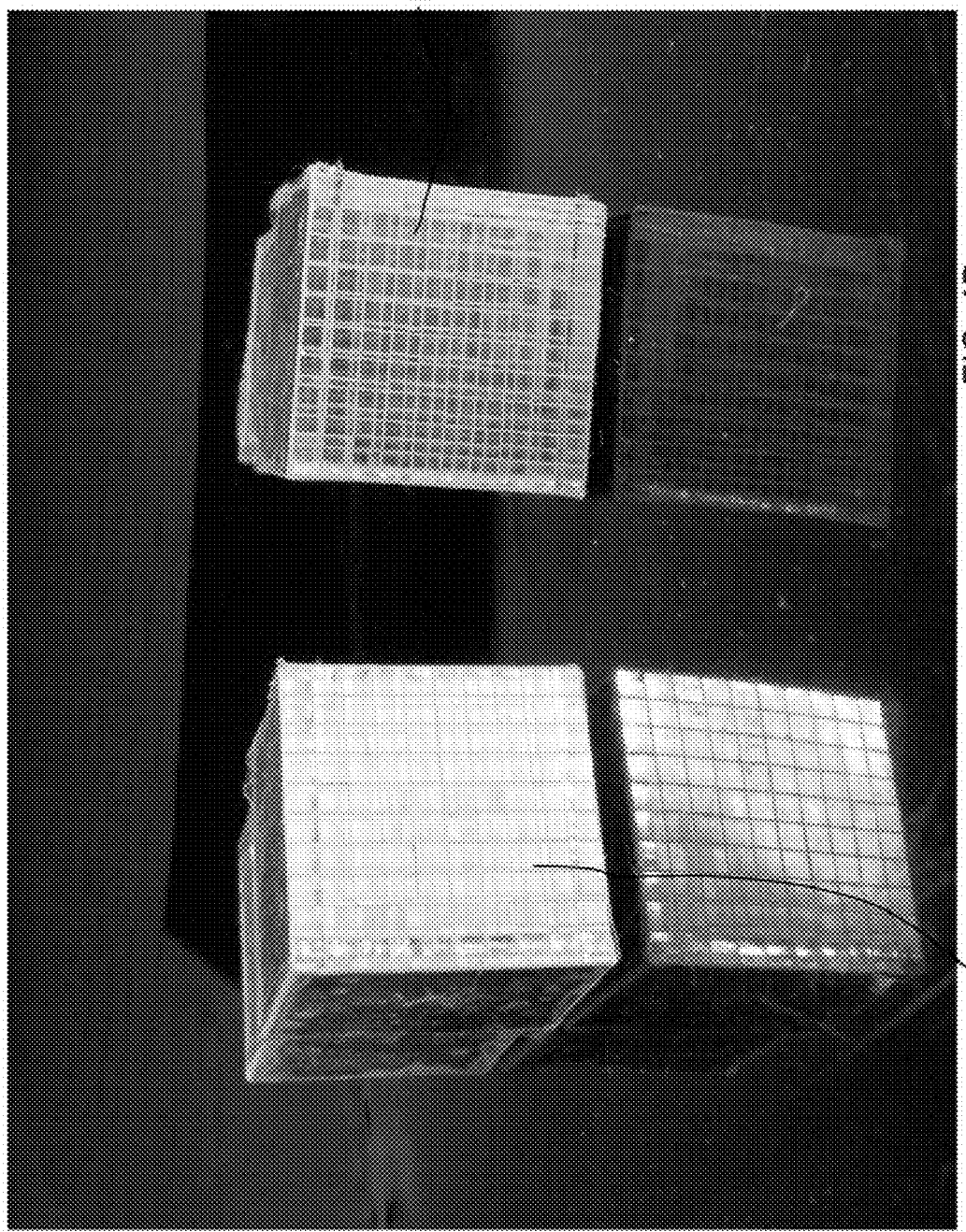

In such imaging, individual detectors can represent individual voxels within a system. In a nonlimiting example the at least one detector 24 in the apparatuses 20, 40, 60 shown in FIGS. 1-3 (or other example systems) includes a plurality of detectors disposed around or substantially around the source 22, e.g., in a ring, cylinder, box, or other arrangement, for receiving the ionizing radiation. The source 22 may be a high energy source (beta, alpha, x-ray, gamma), such as a source of emitted ionizing photons, and in a more particular (nonlimiting) example a positron emitting source within a body, to receive emitted photon pairs in pairs of the plurality of detectors 24. The detectors 24 may include, for example, monolithic or solid state crystals of optical detector material, which may be bonded in a suitable manner and separated by optically interfering material (as a nonlimiting example, the detectors may be tiled into arrays). Nonlimiting example detectors 24 are shown in FIGS. 4A-4B, though the detectors are not intended to be limited to the particular shapes and/or arrangements shown. Any of various shapes and sizes can be used. Nonlimiting examples include cubes, tubes, cylinders, long cylindrical fibers, and long, thin cuboids. A nonlimiting example size is 1 cubic millimeter. The crystals preferably are the same size, though this is not required. The individual crystals may be, for example, ground to a predetermined size and polished, analogous to polishing a solid state laser or scintillation crystal.

Based on the size and location of the crystals, the detectors 24 can absorb ionizing radiation similar to a scintillation crystal. For example, each crystal can represent a voxel in 3D imaging, wherein the size of the crystal determines the spatial sampling of the detector, and the signals can be processed according to known (or to be known) imaging methods, such as but not limited to PET imaging methods. The output probing lights 32 from the detectors (e.g., using output lenses optically coupled to the detectors) may be optically coupled to the comparator 50, 64 either individually (providing individual readout channels) or multiplexed. It is possible to keep the signal from the source of reference light 46, 48 and source of probing light 48 coupled to the comparator 50, 64 entirely within the optical realm.

Figure 11:
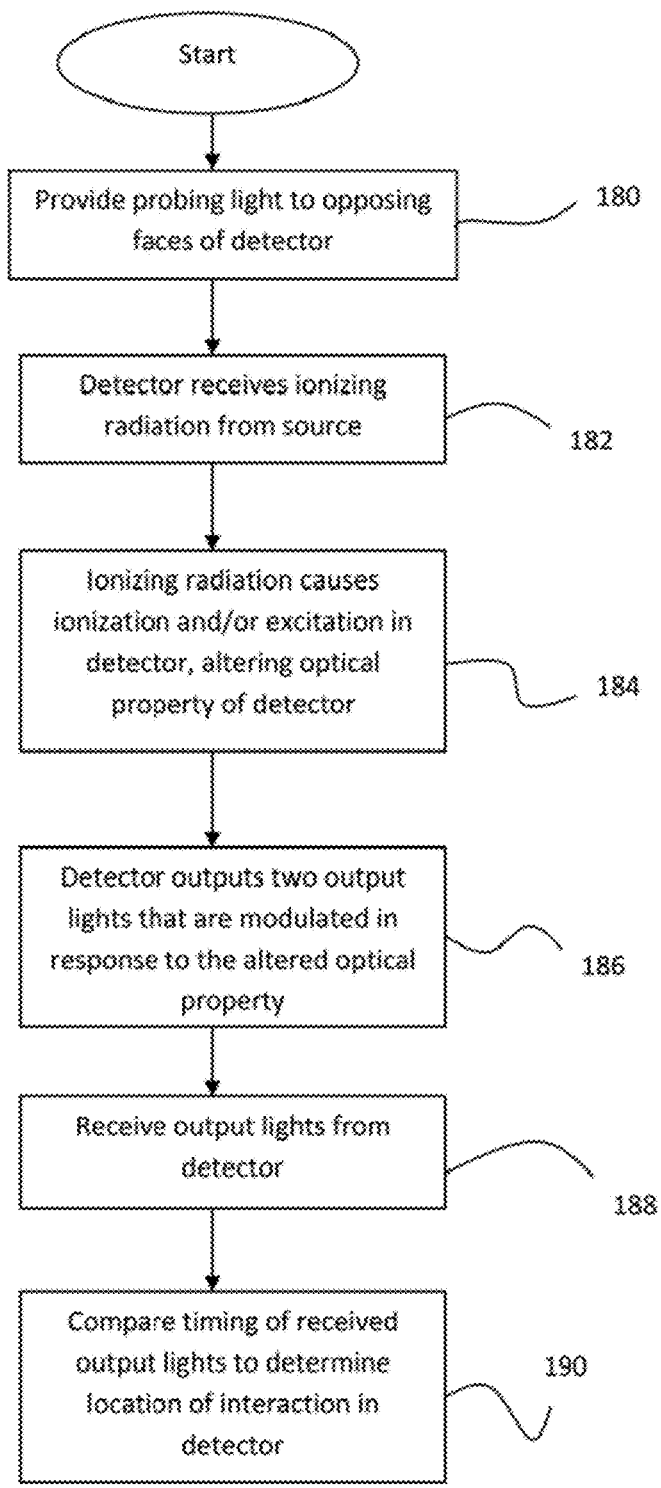
FIG. 11 shows a method for determining the depth or lateral position of a detector interaction.

Alternatively or additionally, providing probing light to opposing faces (e.g., left-right, top-bottom) of the detector 24 as in example methods described above and measuring the corresponding outputs can be used to determine depth or lateral position of a detector interaction based on the timing differences of the light from the opposing faces. For example, as shown in FIG. 11, probing light is provided to opposing faces of a detector (step 180). The detector receives ionizing radiation from a source (step 182), and the ionizing radiation causes ionization and/or excitation in the detector, altering an optical property of the detector (step 184). The detector outputs two output lights that are modulated in response to the altered optical property (step 186). Next, the output lights are received from the detector (step 188), and the timing of the received output lights is compared to determine a location of interaction in the detector (step 190). The improved timing resolution of the detectors 24 in turn provides improved interaction location measurement within the detector and overall improved spatial resolution.

In PET, it is desired to detect photons emitted in coincidence. With the example apparatus 20, 40, 60, either with or without separate precise interaction location determination, the improved time resolution (e.g., on the order of picoseconds versus hundreds of picoseconds) allows the system to follow the line of response (LOR) between two detected photon interactions to essentially pinpoint a precise location of their emission.

Accordingly, in particular example methods of the present invention using the apparatus 20, 40, 60 or other apparatus within the scope of the present invention, pairs of emitted photons are produced from a source of emitted photons, such as source 22. For each photon in the emitted photon pair, the photon is received by the detector 24, and the photon interacts with the detector to cause ionization and/or excitation in the detector. An optical property of the detector is altered in response to the ionization and/or excitation, as described above. The detector 24 is subjected to the probing light 30, 48 and outputs the output probing light 32, 68, and this output light is modulated in response to the altered optical property.

The output light 32, 68 is either detected directly or is compared to the reference light 46, 68 (if reference light is from another detector) to detect a change in the output probing light in response to the photon. A determined photon interaction location is thus determined based on the detection or comparing; e.g., the detector hit represents a voxel for the determined photon interaction location. The pair of photon interaction locations is thus determined, and the emission location can be determined along a line of response (LOR) between the determined pair of photon interactions. The determined emission locations can be combined (as a nonlimiting example, histogrammed) to provide an image. Software algorithms under example embodiments to process the output signals, as will be appreciated by those of ordinary skill in the art. A particular example apparatus and method according to the present invention enables substantially improved time-of-flight (ToF) PET technology, and other applications that require <10 picosecond time resolution temporal correlation between two or more incoming particles (e.g. photons).

Figure 5A:
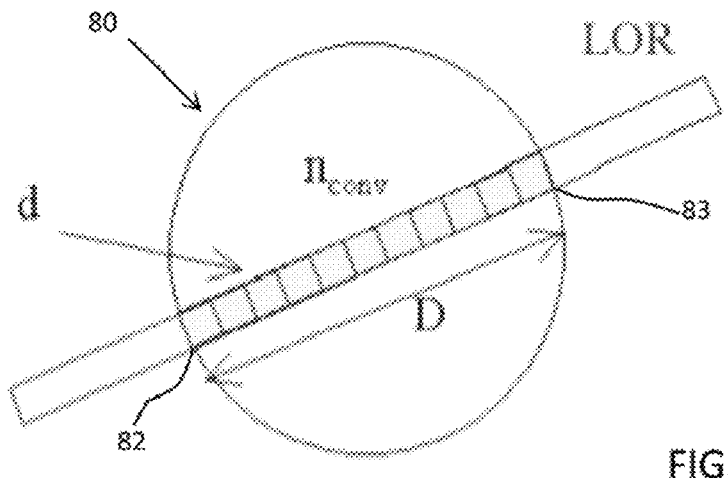
FIGS. 5A-5C shows example image elements contributing to a detector line of response (LOR), where
Figure 5B:
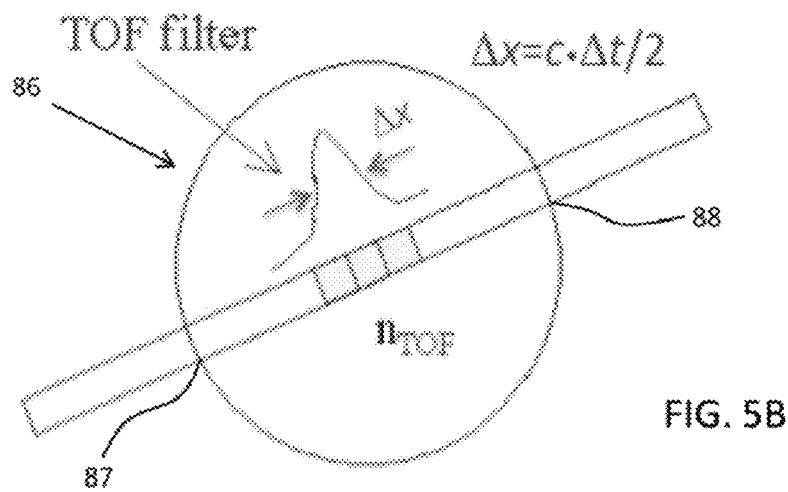
Figure 5C:
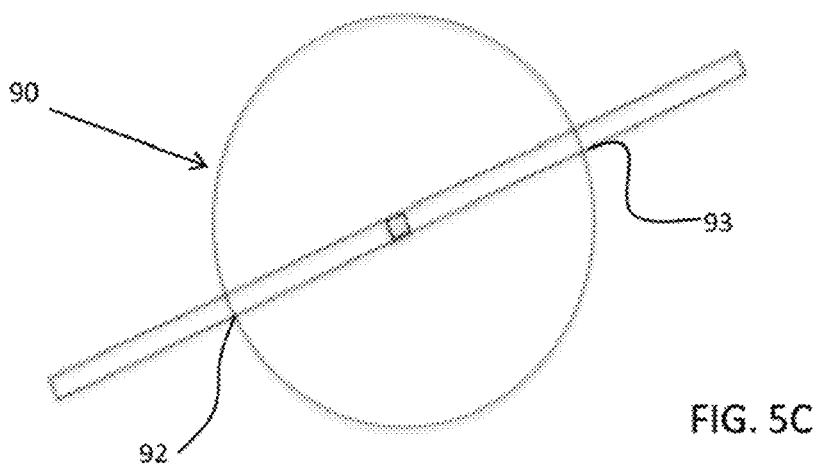

Referring to FIGS. 5A-5C, in a conventional PET system 80 (FIG. 5A), two annihilation photons are emitted from the body and detected nearly simultaneously in two opposing detector elements 82, 83 that localize each photon's point of entry into the system as well as measure their energy and arrival time. If two photons on opposite sides (or substantially opposite sides) of the system arrive within a selected coincidence time window it is assumed that they came from the same positron decay. This coincidence detection process localizes each positron decay event, and thus the molecule of interest, to somewhere along the line of response (LOR) extending between the two detector elements 82, 83. Successively detected coincident photon events are aggregated throughout the PET system 80 for ~30 minutes. Then, mathematical inverse algorithms, typically based on the framework of maximum likelihood estimation maximization, such as ordered-subsets expectation maximization (OSEM), are used to reconstruct three-dimensional (3-D) images of the probe biodistribution that most likely created the pattern of many two-photon hits recorded by the system 80. These algorithms involve computationally intensive hack- and forward line-projection operations along each LOR through the 3-D image volume.

In time-of-flight (ToF) detection, as shown by the example system 86 in FIG. 5B, a scintillation crystal in detector elements 87, 88 creates a tiny cascade of thousands of visible light photons (e.g., blue photons) in response to absorbing a 511 keV annihilation photon interaction. The process is characterized by the crystal's light output (number of light photons created per keV of absorbed energy) and decay constant $\tau$ (ns).

In a PET detector, the scintillation crystal's properties determine how precisely one can say whether two photons are detected simultaneously. The resulting uncertainty in the arrival time difference for the two photons over many events is known as the coincidence time resolution. The scintillation crystal properties are the dominant factor that determines the time resolution: the brighter and faster the light pulse, the better the results.

In ToF-PET, in addition to being able to determine to which LOR the event belongs, the detector coincidence time resolution is sufficient such that by measuring the arrival time difference between the two photons one can constrain the two-photon emission point to a particular segment along the line, as shown in FIG. 5B. The coincidence time resolution directly maps into ToF position uncertainty along the LOR, $\Delta x$, by the formula $\Delta x = c \cdot \Delta t / 2$, where c is the speed of light, and $\Delta t$ is the full-width-at-half-maximum (FWI-IM) time resolution of two detectors in coincidence.

Known ToF scintillation crystals are based on cerium (Ce2+ and Ce3+) activated fluorescence in lanthanum-bromide (LaBr3) and lutetium-yttrium-oxyorthosilicate (LYSO) crystals. One example commercially available ToF-PET system (Philips Gemini TF) has achieved timing resolutions $\Delta t$ of ~500-900 ps ($\Delta x$=7.5-13.5 cm) using LYSO, but these properties tend to drift with time and suffer from count rate limitations.

It is an objective in the art to increase the light output and reduce decay time of scintillation crystal luminescence in order to improve coincidence time resolution. Known Tor-PET systems with $\Delta t$>500 ps time resolution have demonstrated improved lesion contrast and signal-to-noise ratio (SNR) for larger patients. These parameters are improved since during image reconstruction the detected counts are distributed over a much smaller region of each LOR (as shown in FIG. 5B) rather than spreading them with equal probability across the entire LOR (as shown in FIG. 5A). The SNR improvement factor for ToF-PET over conventional PET goes as $\sqrt{(D/\Delta x)}$, where D is the thickness of the patient along a given LOR. So, for example, for a 40 cm length LOR and $\Delta x$=9 cm, the PET image SNR improves by a factor of 2.1. However, for $\Delta x$=7.5-13.5 cm achieved with the Philips Gemini TF, there would be little or no SNR benefit for smaller patients (e.g. D<40 cm thick), and no advantage at all for small animal imaging (e.g. D<6 cm thick).

On the other hand, by providing an example system 90 shown in FIG. 5C with PET detectors 92, 93 according to an embodiment of the present invention employing apparatuses and methods for detecting ionizing radiation, extremely fast timing with low time dispersion (i.e., very high time resolution) can be provided for radiation detection. Photonic materials in example systems can be used instead of scintillation crystals. As a nonlimiting example, such detectors 92, 93 could be provided with (as a nonlimiting example) $\Delta t$=5 ps time resolution, this results in $\Delta x = c \cdot \Delta t/2 = 0.75$ millimeter, over 100-fold smaller than achieved for known ToF PET systems, which translates to over 10-fold increases in SNR. This provides a significant improvement over known PET methodology, as the two-photon emission point for each event can be precisely positioned in one sub-millimeter (e.g., 0.75 mm) voxel along each response line, and computationally intensive iterative tomographic image reconstruction or line-projection operations are not required.

Such a system 90 allows substantial signal amplification (e.g., a greater than 10-fold SNR improvement over existing ToF-PET systems). With the log-order SNR boost, if desired, a patient's injected dose or scan time could be reduced by a factor of ten or more. Alternatively, if desired, ten-fold smaller cross-sectional area detector elements can be used in clinical whole-body PET systems, for narrower LORs (e.g. 2×2 mm$^2$) in the system 90 instead of 6×6 cm$^2$ in the systems 80, 86 to greatly increase spatial resolution. Further, since the light signal is preferably based on bright coherent laser pulses rather than relatively dim scintillation crystal pulses, there is over a log order improvement in photon energy resolution, which enables substantial increases in contrast resolution as well.

Figure 6:
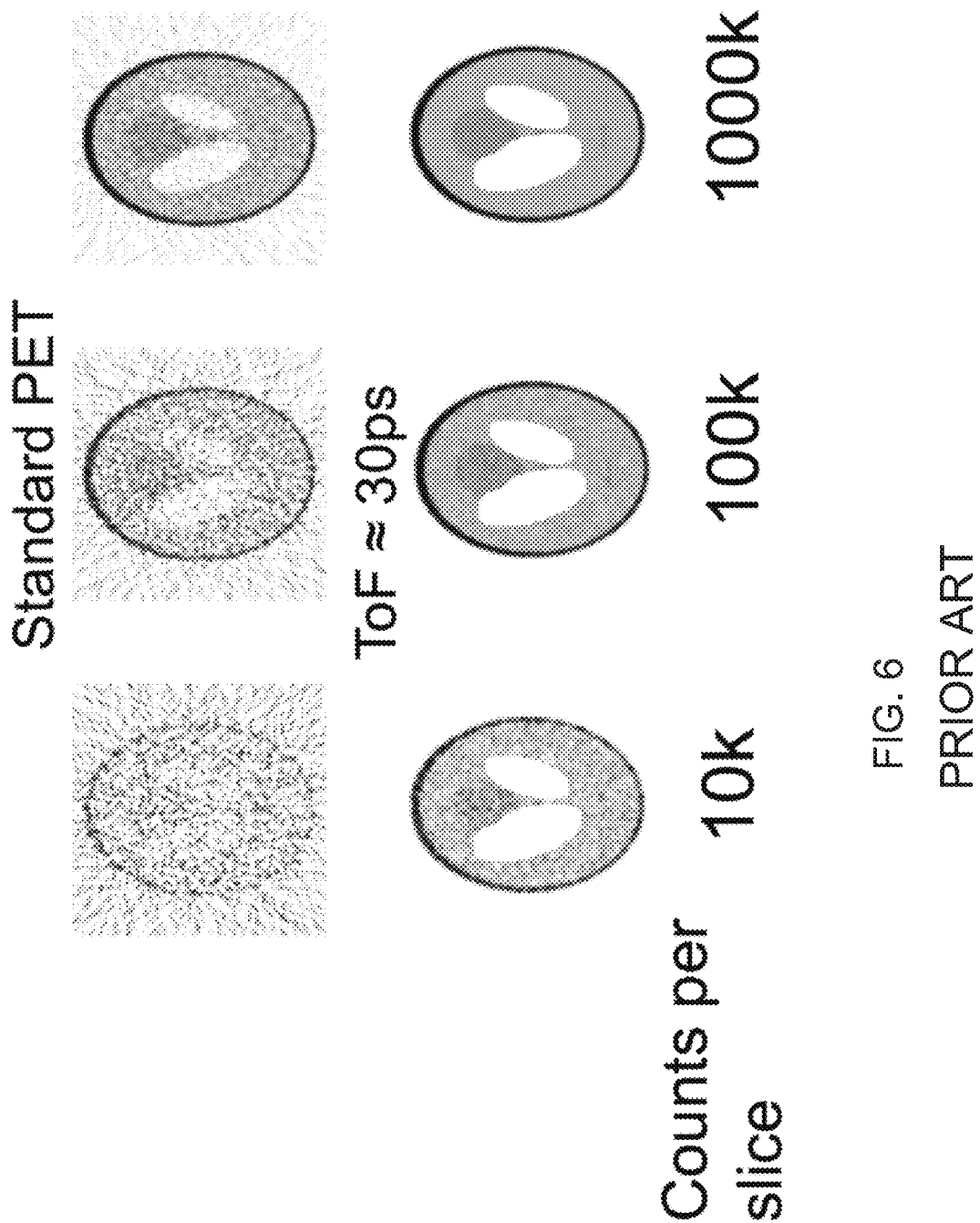
FIG. 6 shows example images produced using standard PET and for ToF ≈30 ps time resolution ToF PET, for 10 k, 100 k, and 1000 k counts per slice.

As a nonlimiting example, FIG. 6 shows example signal-to-noise ratio (SNR) for standard PET and for ToF≈30 ps, at 10, 20, and 30 counts per slice, respectively. As shown, the standard PET exhibits poor SNR, which is caused by very low photon flux and limitations of conventional tomography. By detecting the arrival time of high-energy photons in the picosecond realm, the resulting SNR boost can be used to significantly reduce scan time and patient dose and/or substantially increase spatial resolution. Example methods can improve the time resolution by more than an order of magnitude over conventional ToF PET systems.

A net result of these benefits is to greatly improve PET's ability to visualize and accurately quantify a fewer number of diseased cells. In addition to greatly advancing its accuracy for existing uses in diagnosis, staging and monitoring treatment of disease, the ability to distinguish and quantify a substantially fewer number of diseased cells above background enables PET according to embodiments of the present invention to be further used in clinical management of disease, providing earlier disease detection and management. Furthermore, since an example embodiment image formation process does not require iterative tomographic methods, it can be (as a nonlimiting example) 1000-fold times faster. This allows expanded use of PET for (for instance) real-time imaging applications such as guiding surgical interventions and treatments for disease.

Thus, according to an embodiment of the present invention, nonlinear photonic materials are used for detectors to enable extremely fast detection of radiation. This can provide, as a nonlimiting example, time-of-flight (ToF) positron emission tomography (PET) detectors with 1-10 pico-second (ps) time resolution, as opposed to 500-900 picoseconds achieved by existing PET systems that use scintillation materials for detection of energetic (e.g. 511 kilo-electron-Volt (keV)) photons. This can enable the sub-millimeter localization of a positron decay event along any response line between two annihilation photon detector elements in the system.

In order to achieve 1-10 pico-second (ps) time resolution ToF-PET detectors, an example detector includes nonlinear photonic materials such as those described herein, which can be operated according to the example apparatuses 20, 40, 60 or other methods. Nonlinear photonic materials for a ToF-PET detector can achieve <10 ps time resolution, as opposed to scintillation crystals, which currently can at best achieve hundreds of ps time resolution in optimized laboratory experiments. Pico-second time resolution is known in nonlinear optics, e.g., with transitions as fast as <1 ps. As one nonlimiting example, high Z, high density platinum-bridged halide compounds can be provided for picosecond ToF photon detection.

As a nonlimiting example, nonlinear photonic materials can be provided that undergo photon-induced phase change. These optical transitions can occur in picoseconds, and can be induced by excitation from a very few number of electrons or photons. A nonlimiting example of an optical transition that can be used is reflectivity (though other types of optical transitions are possible, as disclosed herein). If the reflectivity of the crystal is "switched" as a result of a 511 keV photon interaction (photoelectric effect or Compton scatter) in the material, which produces on the order of $10^4$-$10^5$ electron-hole pairs plus significant vibrational energy (phonons), and this transition occurs within pico-seconds, ToF-PET with 1-10 picosecond resolution is possible.

Because the reflectivity can change in the picosecond realm, high energy photon interactions can be measured by monitoring the reflections using a coherent light source, as described in example methods herein. These fast optical transitions can be detected using, for instance, all-optical photonic circuits, which are much faster than electronic circuits.

Particular nonlimiting example materials used in embodiments of the present invention for ultrafast 511 keV photon detection in ToF PET are capable of producing ultra-fast optical phase transitions that are high-Z and high-density in order to efficiently absorb highly-penetrating 511 keV photons. These include, for instance, suitable photo-induced phase changing materials, such as in a quasi-one-dimensional Br-bridged Pd compound, non-linear photonic materials in other candidate meta-stable Mott insulators, and non-linear photonic materials based on nano-photonic crystals. Also, high Z quantum-confined Stark effect electro-optical modulators can also be capable of ultra-fast optical absorption modulation. Further, such materials preferably (though not necessarily) can be formed into large volume and inexpensive crystals.

Figure 7:
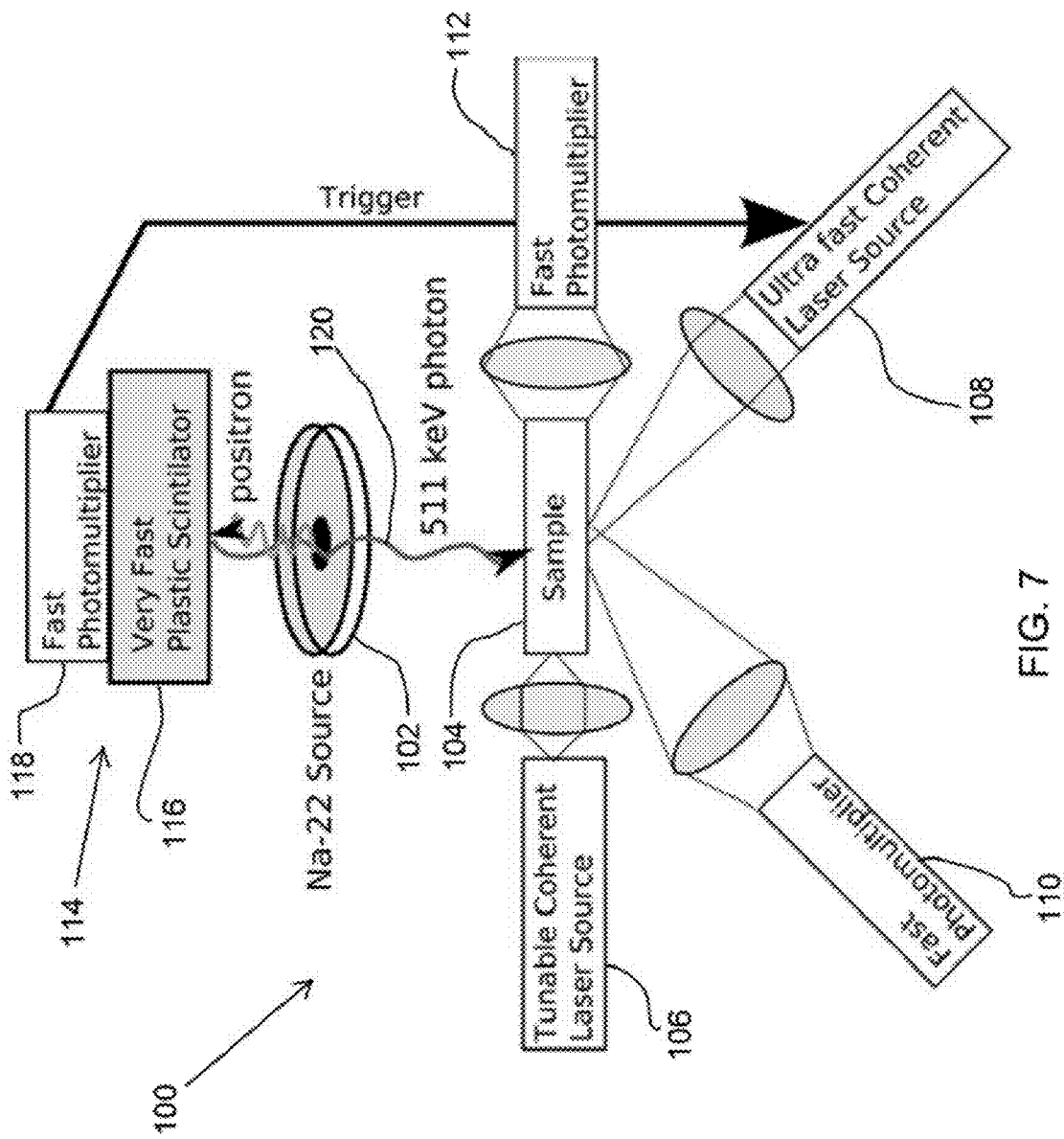
FIG. 7 shows an example optical test bed for evaluating non-linear optical samples for use in an apparatus for detecting ionizing radiation.

Referring to FIG. 7, an optical test bed 100 is provided according to example embodiments of the invention to probe and characterize induced changes in non-linear photonic materials in the pico-second realm. A $^{22}$Na 511 keV photon source 102, or other high frequency source, pumps a sample 104. Reflective and transmission temporal properties (for example) of the sample 104 are probed by a tunable coherent continuous wave laser 106. Phase state properties are probed by a triggered ultra-fast coherent light source 108, which in an example embodiment is provided by a mode locked Ti: sapphire laser. Fast photomultipliers 110, 112 are used to detect the light signal in both cases. A scintillation detector 114, including a fast scintillator 116 and a fast photomultiplier 118, provides a fast coincidence trigger for the probing laser 108. In an example operation, the candidate material sample 104 is irradiated with annihilation photons 120, and the intensity and temporal properties of a modulated optical signal are measured using the optical test bed 100.

Using photonic crystal detector materials according to example embodiments of the present invention allows very fast, e.g., <10 ps, time resolution ToF PET systems. Additionally, photonic (e.g., nonlinear photonic) crystals can provide extremely fast, all-optical coincidence processing of PET signals that preserves <10 ps time resolution. According to example embodiments of the present invention, ultra-fast all-optical PET detectors are provided that do not require photodetectors or conversion of the light pulse to an electronic signal, and can provide fast optical transitions for ToF PET. Example methods are also provided to process these rapid transitions.

Standard PET electronics may not have optimal capability to probe the extremely fast optical properties of certain materials as used in particular detectors. In example embodiments, the <10 ps optical transitions are detected using all-optical photonic circuits which can be much faster, reliable, and/or less expensive than electronic signal processing circuits.

An example embodiment employs an optical-only logic processing circuit using nano-photonic crystals. Using nano-photonic circuits allows one to replace electronic logic and can achieve ultra-fast processing of optical signals. Example nano-photonic circuits are disclosed, as one example; in R. M. Osgood, et al., Engineering nonlinearities in nanoscale optical systems, physics and applications in dispersion-engineered silicon nanophotonic wires, Adv. Opt. Photon. 1, 162-235 (2009), which is incorporated in its entirety herein by reference.

Figure 8:
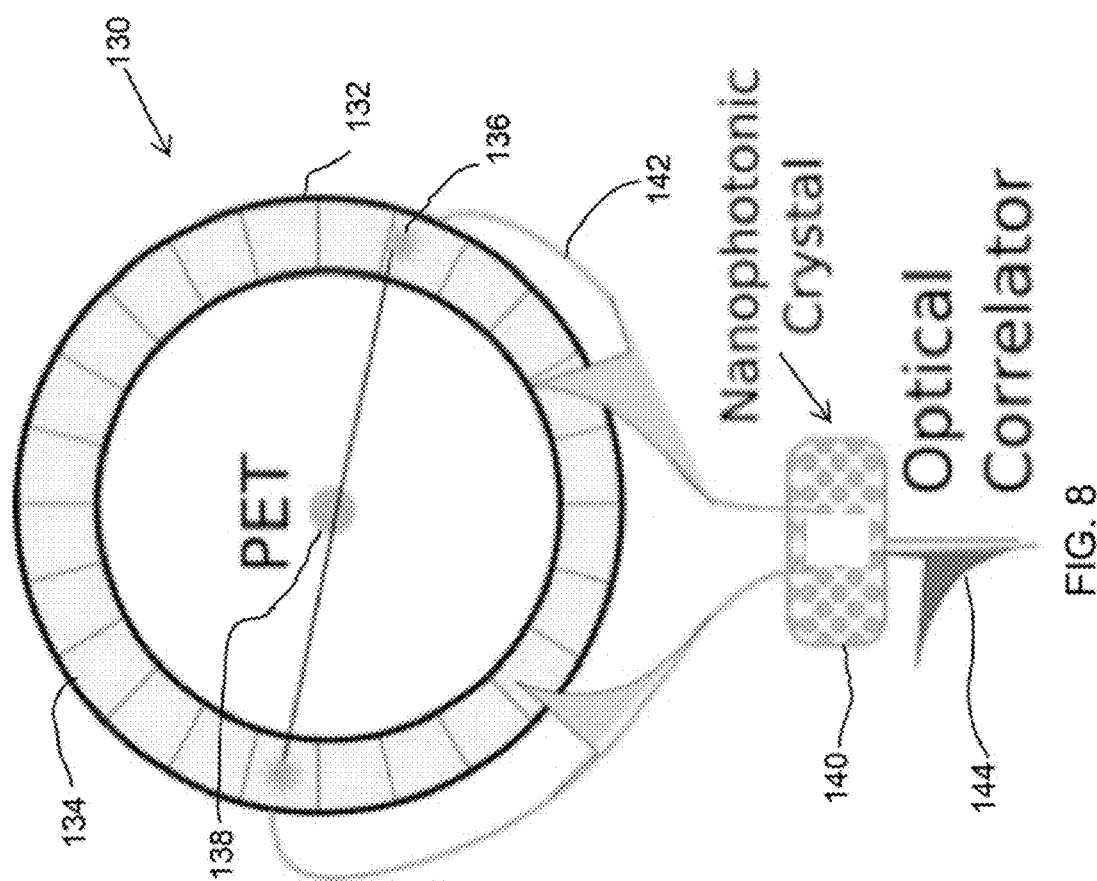
FIG. 8 shows an example apparatus for PET using nanophotonic crystals for optical temporal correlation of the coincident 511 keV photons, according to an embodiment of the present invention.

A typical PET apparatus correlates the timing of a multitude of signals. To this end, nano-photonic temporal correlators are provided in example embodiments of the present invention for coincidence photon pairing in PET. FIG. 8 shows an example optical PET system 130 including a ring 132 of photonic crystal detectors 134, disposed to receive emitted photons 136 from a source 138, and a nano-photonic crystal 140 with an engineered defect for use as an all optical correlator for PET signals. The photon signal from the PET detector 134 is converted to a fast coherent optical signal confined to an optical fiber 142. The fibers 142 are run to optical temporal correlators 144. These circuits can identify temporal coincidence of two photons optically (preferably, without using photodetectors or electronics).

Figure 9A:
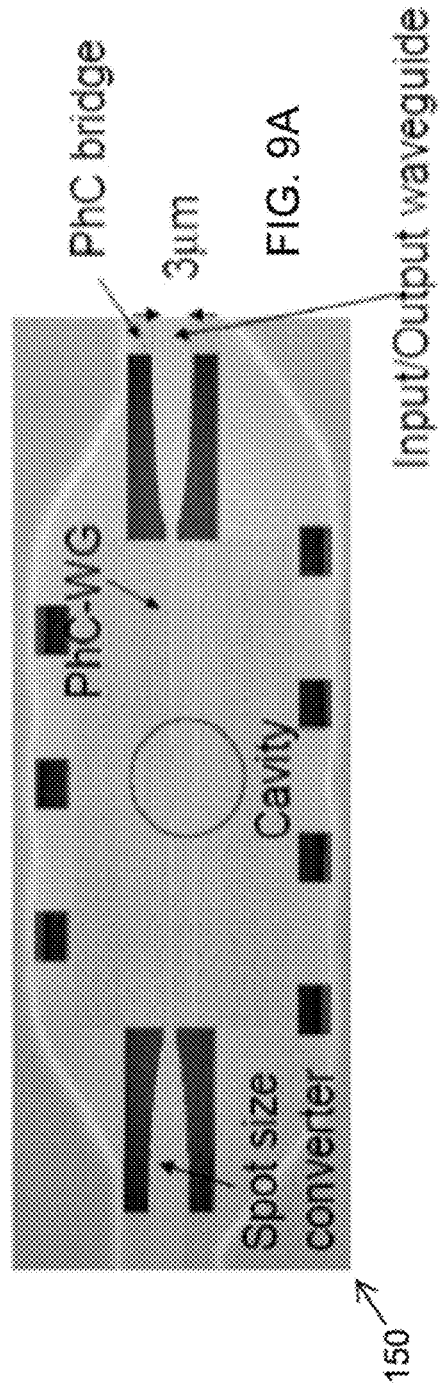
FIGS. 9A-9C show a non-photonic flip-flop for use with an optical temporal correlator for PET signals from photonic crystal detectors, where
Figure 9B:
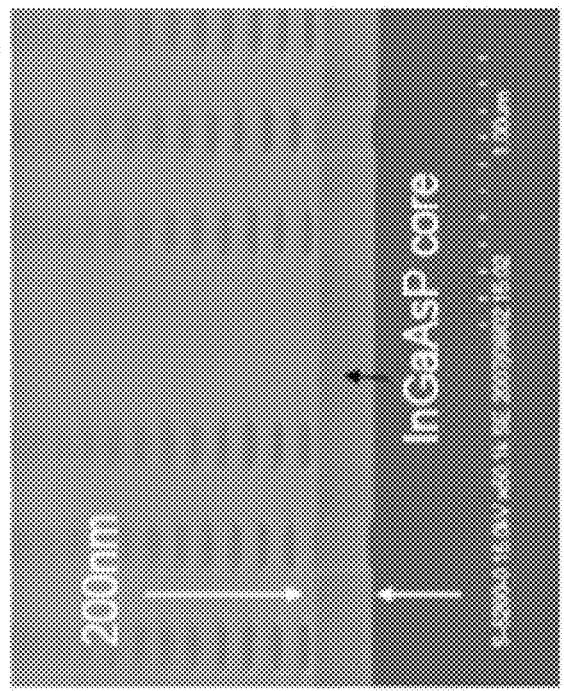
Figure 9C:
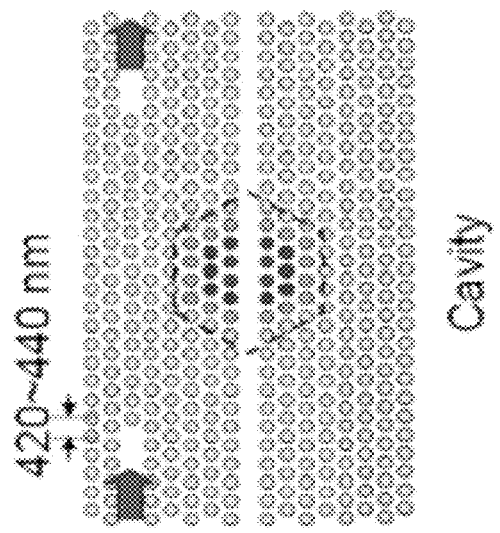

FIGS. 9A-9C show a nano-photonic ultra-fast flip-flop 150 that can be used as an optical temporal correlator for PET signals for photonic crystal detectors. An example nano-photonic flip-flop is disclosed in Akihiko Shinya, et al., "All-optical on-chip bit memory based on ultra high Q InGaAsP photonic crystal," Opt. Express 16, 19382-19387 (2008), which is incorporated in its entirety by reference herein. The example nano-photonic flip-flop 150 includes a fabricated 1.3 μm-InGaAsP core PhC on InP substrate. The example core thickness and air hole diameter are 200 and 2000 nm, respectively. The lattice constraints are 420-440 nm. In FIG. 9A, air holes surrounding a cavity (circled) are shifted away from the center of the line defect by distances of 9, 6, and 3, respectively. The nano-photonic ultra-fast flip flop 150 can be used to capture the time difference between PET photon pulses with ps precision.

Apparatuses and methods are provided herein for detecting ionizing radiation according to embodiments of the present invention. Imaging methods and systems are also provided, including example methods and systems using PET, and more particularly employing ToF PET. PET plays a major role in pre-clinical cancer research, as well as the clinical management of cancer. Thus, technological advances that lead to substantial enhancement in PET's performance can be of great benefit. Example embodiments and methods of the present invention provide picosecond ToF PET, which can greatly improve clinical as well as small animal imaging by significantly increasing spatial resolution, contrast resolution, effective photon sensitivity, and SNR by an order of magnitude. Time-of-flight capabilities in example methods and systems can effectively increase photon sensitivity, because the reconstruction need not entail an inverse radon transform problem inherent to projection tomography, but rather enables direct position encoding at one point along the line-of-response. While conventional ToF PET is limited by photon arrival time resolution of 511 keV photon detectors, example methods and systems of the present invention can improve (e.g., by two orders of magnitude) the time resolution of these detectors.

Providing improved ionizing radiation detection systems and methods, and imaging systems and methods, according to embodiments of the present invention can substantially enhance visualization and quantification of molecular processes associated with cancer on millimeter scales in clinical patients, rather than the centimeter scales currently available. Such systems and methods can also help to advance the development of new imaging (e.g., PET imaging) probes and assays for understanding the molecular-basis of cancer and guiding the development of novel cancer treatments.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. An apparatus for imaging comprising:
a source of emitted photons having an energy of at least 1 keV;
a plurality of detectors disposed relative to the source to receive the emitted photons, the emitted photons interacting with said detectors to cause ionization and/or excitation in said detectors, wherein an optical property of said detectors is altered in response to the ionization and/or excitation produced from the emitted photons;

a source of reference light;

a source of probing light disposed relative to each of said detectors to probe said detectors, wherein said detectors output the probing light, wherein the output light is modulated in response to the altered optical property;

a comparator for comparing the reference light and the probing light for each of said detectors, said comparator providing an output pulse based on a change between the reference light and the probing light; and a receiver for receiving the one or more output pulses from said comparator and for each output pulse, determining whether the emitted photon interacted with the detector, including an identification of a particular detector hit, and determining at least one of an energy or time of the emitted photon;

said receiver being configured to detect an emitted pair of photons based on receiving a pair of output pulses and to determine an event location from said detected emitted pair of photons.

2. The apparatus of claim 1 wherein the source of probing light comprises a source of coherent probing light and the source of reference light comprises a source of coherent reference light.

3. The apparatus of claim 2, wherein said comparator comprises an interferometer coupled to said source of reference light and to said detector for receiving the output light.

4. A method for detecting ionizing radiation, the ionizing radiation comprising one or more individual particles, the method comprising:

subjecting at least one detector to a probing light, wherein the detector outputs the probing light;

providing one or more individual ionizing radiation particles having an energy of at least 1 keV to interact with the detector and cause ionization in the detector, wherein an optical property of the detector is altered in response to the ionization produced from the individual ionizing radiation particle;

for each individual ionizing radiation particle, comparing the output probing light to a reference light to detect a change in the output probing light in response to the provided ionizing radiation particle, and determining at least one of energy or arrival time of the ionizing radiation particle;

wherein the at least one detector comprises a plurality of detectors, and further comprising:

recording which pair of detectors interact with the pair of individual ionizing radiation particles and a pair of interaction times;

determining a location for the emission point of each ionizing radiation particle based on said recorded pair of detectors and interaction times.

5. The method of claim 4, further comprising:

imaging a subject based on said determining a location over many emission events.

6. A method of imaging comprising;

producing pairs of emitted photons from a source of emitted photons;

determining an emission location for each of the pairs of emitted photons;

combining said determined emission locations to provide an image;

wherein said determining an emission location comprises:
 determining a pair of photon interaction locations; and
 determining the emission location along a line of response between said determined pair of photon interactions;

wherein said determining a pair of photon interaction locations comprises, for each photon in an emitted photon pair:

receiving the photon by a detector, the photon interacting with the detector to cause ionization and/or excitation in the detector, wherein an optical property of the detector is altered in response to the ionization and/or excitation;

subjecting the detector to a probing light, wherein the detector outputs the probing light, wherein the output light is modulated in response to the altered optical property;

comparing the output probing light to a reference light to detect a change in the output probing light in response to the photon; and determining a photon interaction location based on said comparing.

7. The method of claim 6, wherein said determining the emission location comprises:

determining the line of response between said determined photon interaction locations;

calculating the emission location as a point along the determined line of response based on said determined line of response and the speed of the emitted photons.

8. The method of claim 7, further comprising:

aggregating said determined emission locations; and processing said aggregated emission locations to provide the image.

* * * * *